United States Patent
Tarnava et al.

(10) Patent No.: US 11,266,169 B2
(45) Date of Patent: *Mar. 8, 2022

(54) COMPOSITION FOR PRODUCING HYDROGEN RICH WATER AND OTHER PRODUCTS

(71) Applicant: H2 Water Technologies Ltd., Vancouver (CA)

(72) Inventors: Alexander Tarnava, Coquitlam (CA); Richard James Holland, Vancouver (CA)

(73) Assignee: H2 Water Technologies Ltd., Vancouver (CA)

(*) Notice: Subject to any disclaimer, the term of this patent is extended or adjusted under 35 U.S.C. 154(b) by 0 days.

This patent is subject to a terminal disclaimer.

(21) Appl. No.: 16/256,389

(22) Filed: Jan. 24, 2019

(65) Prior Publication Data
US 2019/0166885 A1    Jun. 6, 2019

Related U.S. Application Data

(63) Continuation of application No. 16/317,765, filed as application No. PCT/IB2017/001067 on Jul. 17, 2017.

(60) Provisional application No. 62/362,841, filed on Jul. 15, 2016.

(51) Int. Cl.

| | |
|---|---|
| A23L 2/40 | (2006.01) |
| A23L 2/395 | (2006.01) |
| A23L 2/56 | (2006.01) |
| A23L 2/68 | (2006.01) |
| A23L 33/16 | (2016.01) |
| A23L 2/39 | (2006.01) |
| A61K 8/19 | (2006.01) |
| A61K 8/362 | (2006.01) |
| A61K 33/00 | (2006.01) |
| C01B 3/08 | (2006.01) |
| A23L 2/54 | (2006.01) |
| A61K 9/00 | (2006.01) |
| A61K 45/06 | (2006.01) |
| A61K 31/194 | (2006.01) |
| A61K 33/06 | (2006.01) |
| A61K 9/20 | (2006.01) |
| A61K 47/12 | (2006.01) |

(52) U.S. Cl.
CPC .................. *A23L 2/40* (2013.01); *A23L 2/39* (2013.01); *A23L 2/395* (2013.01); *A23L 2/54* (2013.01); *A23L 2/56* (2013.01); *A23L 2/68* (2013.01); *A23L 33/16* (2016.08); *A61K 8/19* (2013.01); *A61K 8/362* (2013.01); *A61K 9/00* (2013.01); *A61K 9/0095* (2013.01); *A61K 31/194* (2013.01); *A61K 33/00* (2013.01); *A61K 33/06* (2013.01); *A61K 45/06* (2013.01); *C01B 3/08* (2013.01); *A23V 2002/00* (2013.01); *A23V 2200/15* (2013.01); *A23V 2200/21* (2013.01); *A23V 2250/044* (2013.01); *A23V 2250/056* (2013.01); *A23V 2250/1578* (2013.01); *A23V 2250/161* (2013.01); *A23V 2250/1886* (2013.01); *A23V 2250/61* (2013.01); *A61K 9/2013* (2013.01); *A61K 47/12* (2013.01); *A61K 2800/87* (2013.01); *Y02E 60/36* (2013.01)

(58) Field of Classification Search
CPC ...................................................... A61K 33/00
See application file for complete search history.

(56) References Cited

U.S. PATENT DOCUMENTS

| | | | |
|---|---|---|---|
| 5,151,274 A * | 9/1992 | Saltman ................ | A61K 33/24 424/630 |
| 5,843,477 A | 12/1998 | Alexander | |
| 6,303,147 B1 * | 10/2001 | Gilis ................... | A61K 9/2013 424/484 |
| 7,189,330 B2 | 3/2007 | Hayashi et al. | |
| 9,144,581 B2 | 9/2015 | Miljkovic | |
| 9,149,774 B2 | 10/2015 | Satoh et al. | |
| 2004/0265380 A1 * | 12/2004 | Delmas ............... | A61K 9/0007 424/466 |

(Continued)

FOREIGN PATENT DOCUMENTS

| | | |
|---|---|---|
| CA | 1051779 A | 4/1979 |
| CA | 2847292 A1 | 1/2013 |

(Continued)

OTHER PUBLICATIONS

Chowhan (Journal of pharmaceutical sciences. Jun. 1986;75(6):542-5).*

(Continued)

*Primary Examiner* — Sarah Alawadi
(74) *Attorney, Agent, or Firm* — Clark & Elbing LLP

(57) ABSTRACT

The invention provides compositions for producing hydrogen rich water, nutraceuticals, cosmetics, pharmaceuticals, and other products. In one embodiment, the invention provides a composition, e.g., a tablet, including magnesium metal, at least one water-soluble acid, and a binding agent. The magnesium metal and at least one water-soluble acid may be present in amounts sufficient to maintain a pH of less than 7, e.g., at a specific time period after reaction, and a concentration of at least 0.5 mM $H_2$ after reaction in 50 mL water in a container e.g., a sealed or an open container, e.g., at least 0.5 mM $H_2$ after reaction in 100 mL water or at least 0.5 mM $H_2$ after reaction in 500 mL water. The composition may also include a lubricant.

16 Claims, No Drawings

(56) References Cited

U.S. PATENT DOCUMENTS

| | | | |
|---|---|---|---|
| 2008/0311225 | A1 | 12/2008 | Shiga |
| 2010/0316776 | A1 | 12/2010 | Miljkovic |
| 2015/0132359 | A1 | 5/2015 | Miljkovic |
| 2015/0258136 | A1 | 9/2015 | Lucas |
| 2016/0113865 | A1 | 4/2016 | Kazakevitch et al. |
| 2019/0290682 | A1 | 9/2019 | Tarnava et al. |

FOREIGN PATENT DOCUMENTS

| | | | |
|---|---|---|---|
| CA | 2951287 | A1 | 12/2015 |
| CA | 2984379 | A1 | 11/2016 |
| CN | 1228706 | A | 9/1999 |
| JP | 2007-230964 | A | 9/2007 |
| JP | 2012-19739 | A | 2/2012 |
| JP | 2015-205791 | A | 11/2015 |
| RU | 2530122 | C1 | 10/2014 |
| RU | 2014124263 | A | 12/2015 |
| WO | WO-2006/098405 | A1 | 9/2006 |
| WO | WO 2016/079265 | * | 11/2015 |
| WO | WO-2017/070647 | A1 | 4/2017 |
| WO | WO-2017/192755 | A1 | 11/2017 |

OTHER PUBLICATIONS

Copley (https://web.archive.org/web/20141218171647/https://www.copleyscientific.com/home/pharmaceutical-testing/friability-testing/introduction-to-friability-testing; Dec. 18, 2014).*

Machine translation of JP2015-205791A (Nov. 19, 2015).*

Sigma Aldrich. Particle Size Conversion Table (for mesh sizes). Retrieved (Year: 2010).*

U.S. Appl. No. 16/317,765, Tarnava et al.

"'Hydrogen water' to drink, made in containers and made with a generator—'Hydrogen water' has no official definition, etc., and the dissolved hydrogen concentration varies," National Consumer Affairs Center of Japan, <http://www.kokusen.go.jp/news/data/n-20161215_2.html>, published Dec. 15, 2016, retrieved Mar. 28, 2019 (22 pages).

Azuma et al., "Drinking hydrogen-rich water has additive effects on non-surgical periodontal treatment of improving periodontitis: a pilot study," Antioxidants (Basel). 4(3):513-22 (2015).

Chandrasekaran et al., "Permeation of topically applied magnesium ions through human skin is facilitated by hair follicles," Magnes Res. 29(2):35-42 (2016).

Chuai et al., "Hydrogen-rich saline attenuates radiation-induced male germ cell loss in mice through reducing hydroxyl radicals," Biochem J. 442(1):49-56 (2012).

Dixon et al., "The evolution of molecular hydrogen: a noteworthy potential therapy with clinical significance," Med Gas Res. 3(1):10 (2013) (12 pages).

Dole et al., "Hyperbaric hydrogen therapy: a possible treatment for cancer," Science. 190(4210):152-4 (1975) (4 pages).

Ichihara et al., "Beneficial biological effects and the underlying mechanisms of molecular hydrogen—comprehensive review of 321 original articles," Med Gas Res. 5:12 (2015) (21 pages).

Ignacio et al., "The balneotherapy effect of hydrogen reduced water on UVB-mediated skin injury in hairless mice," Mol Cell Toxicol. 9(1):15-21 (2013).

Ignacio et al., "The drinking effect of hydrogen water on atopic dermatitis induced by *Dermatophagoides farinae* allergen in NC/Nga mice," Evid Based Complement Alternat Med. 2013:538673 (2013) (5 pages).

International Search Report and Written Opinion for International Patent Application No. PCT/IB2017/001067, dated Dec. 18, 2017 (9 pages).

Ishibashi et al., "Consumption of water containing a high concentration of molecular hydrogen reduces oxidative stress and disease activity in patients with rheumatoid arthritis: an open-label pilot study," Med Gas Res. 2(1):27 (2012) (8 pages).

Ishibashi et al., "Therapeutic efficacy of infused molecular hydrogen in saline on rheumatoid arthritis: a randomized, double-blind, placebo-controlled pilot study," Int Immunopharmacol. 21(2):468-73 (2014).

Ito et al., "Drinking hydrogen water and intermittent hydrogen gas exposure, but not lactulose or continuous hydrogen gas exposure, prevent 6-hydorxydopamine-induced Parkinson's disease in rats," Med Gas Res. 2(1):15 (2012) (7 pages).

Iuchi et al., "Molecular hydrogen regulates gene expression by modifying the free radical chain reaction-dependent generation of oxidized phospholipid mediators," Sci Rep. 6:18971 (2016) (12 pages).

Kato et al., "Hydrogen-rich electrolyzed warm water represses wrinkle formation against UVA ray together with type-I collagen production and oxidative-stress diminishment in fibroblasts and cell-injury prevention in keratinocytes," J Photochem Photobio B. 106:24-33 (2012).

Lambers et al., "Natural skin surface pH is on average below 5, which is beneficial for its resident flora," Int J Cosmet Sci. 28(5):359-70 (2006).

Matsumoto et al., "Oral 'hydrogen water' induces neuroprotective ghrelin secretion in mice," Sci Rep. 3:3273 (2013) (5 pages).

Nakao et al., "Effectiveness of hydrogen rich water on antioxidant status of subjects with potential metabolic syndrome—an open label pilot study," J Clin Biochem Nutr. 46(2):140-9 (2010).

Nicolson et al., "Clinical effects of hydrogen administration: from animal and human diseases to exercise medicine," Int J Clin Med. 7(1):32-76 (2016).

Ohsawa et al., "Hydrogen acts as a therapeutic antioxidant by selectively reducing cytotoxic oxygen radicals," Nat Med. 13(6):688-94 (2007).

Tomofuji et al., "Effects of hydrogen-rich water on aging periodontal tissues in rats," Sci Rep. 4:5534 (2014) (6 pages).

Xia et al., "Effect of hydrogen-rich water on oxidative stress, liver function, and viral load in patients with chronic hepatitis B," Clin Transl Sci. 6(5):372-5 (2013).

Yoon et al., "Positive effects of hydrogen water on 2,4-dinitrochlorobenzene-induced atopic dermatitis in NC/Nga mice," Biol Pharm Bull. 37(9):1480-5 (2014).

Yoritaka et al., "A randomized double-blind multi-center trial of hydrogen water for Parkinson's disease: protocol and baseline characteristics," BMC Neurol. 16:66 (2016) (4 pages).

Yoritaka et al., "Pilot study of $H_2$ therapy in Parkinson's disease: A randomized double-blind placebo-controlled trial," Mov Disord. 28(6):836-9 (2013).

Zhang et al., "Effects of hydrogen-rich water on depressive-like behavior in mice," Sci Rep. 6:23742 (2016) (7 pages).

Chowanadisai et al., "Pyrroloquinoline quinone stimulates mitochondrial biogenesis through cAMP response element-binding protein phosphorylation and increased PGC-1alpha expression," J Biol Chem. 285(1):142-52 (2010).

Imai et al., "$NAD^+$ and sirtuins in aging and disease," Trends Cell Biol. 24(8):464-71 (2014).

Mouchiroud et al., "$NAD^+$ metabolism: a therapeutic target for age-related metabolic disease," Crit Rev Biochem Mol Biol. 48(4):397-408 (2013) (13 pages).

Ohta, "Molecular hydrogen as a preventive and therapeutic medical gas: initiation, development and potential of hydrogen medicine," Pharmacol Ther. 144(1):1-11 (2014).

Ostojic, "Targeting molecular hydrogen to mitochondria: barriers and gateways," Pharmacol Res. 94:51-3 (2015).

Tao et al., "Pyrroloquinoline quinone preserves mitochondrial function and prevents oxidative injury in adult rat cardiac myocytes," available in PMC Mar. 23, 2010, published in final edited form as: Biochem Biophys Res Commun. 363(2):257-62 (2007) (12 pages).

Sakai et al., "Consumption of water containing over 3.5 mg of dissolved hydrogen could improve vascular endothelial function," Vasc Health Risk Manag. 10:591-7 (2014).

Muzikova et al., "A study of micronized poloxamers as lubricants in direct compression of tablets," Acta Pol Pharm. 70(6):1087-96 (2013).

(56) References Cited

OTHER PUBLICATIONS

Ostojic et al., "28-days hydrogen-rich water supplementation affects exercise capacity in mid-age overweight women: 2942 Board #225 Jun. 1 330 PM-500 PM," Med Sci Sports Exerc. 50(5S):728-9 (2018).
LeBaron et al., "Acute supplementation with molecular hydrogen benefits submaximal exercise indices. Randomized, double-blinded, placebo-controlled crossover pilot study," J Lifestyle Med. 9(1):36-43 (2019).
H2 Sciences Inc., "Measuring dissolved $H_2$ in water produced using 'open glass' $H_2$ tablets," <https://www.h2sciencesinc.com/open-glass.html>, retrieved on Apr. 24, 2019 (2 pages).
Purative, "Active H-minus," created Jun. 16, 2011 (2 pages).
"How to Use Active H-minus," created Dec. 5, 2011 (2 pages).
$H_2$ Water Technologies Ltd., Transcript of H2 Water Technologies Ltd. YouTube video: "Welcome to the Movement—Drink HRW," <https://www.youtube.com/watch?v=-allBP4e3I0>, published Nov. 4, 2016 (1 page).
$H_2$ Water Technologies Ltd., Transcript of $H_2$ Water Technologies Ltd. YouTube video: "Preparing Your Drink HRW Rejuvination Water," <https://www.youtube.com/watch?v=5exhdqsjC4c>, published Nov. 4, 2016 (2 pages).
$H_2$ Water Technologies Ltd., Transcript of $H_2$ Water Technologies Ltd. YouTube video: "$H_2$ Blue Tests Drink HRW Rejuvenation," <https://www.youtube.com/watch?v=DZrGiLyVHqs>, published Nov. 4, 2016 (1 page).
Korovljev et al., "Molecular hydrogen affects body composition, metabolic profiles, and mitochondrial function in middle-aged overweight women," Ir J Med Sci. 187(1):85-9 (2018). doi: 10.1007/s11845-017-1638-4.
Extended European Search Report for European Patent Application No. 17827064.1, dated Mar. 13, 2020 (9 pages).
Safonov et al., "Hydrogen nanobubbles in a water solution of dietary supplement," Colloids Surf A Physicochem Eng Asp. 436: 333-6 (2013) (3 pages).
Official Action for Russian Application No. 2019103568, dated Oct. 23, 2020 (12 pages).
Search Report for Russian Application No. 2019103568, dated Oct. 23, 2020 (4 pages).

\* cited by examiner

COMPOSITION FOR PRODUCING HYDROGEN RICH WATER AND OTHER PRODUCTS

BACKGROUND OF THE INVENTION

Molecular hydrogen has been found to be of potential therapeutic use for a variety of diseases injuries. For example, $H_2$ has been shown to have applications as a method for reducing wrinkles in the skin (*J. Photochem. Photobiol. B.* 2012; 106:24-33), treating atopic dermatitis (*Evid. Based Complement. Alternat. Med.* 2013; 2013: 538673), and as a post-treatment regimen for radiation therapies (*Biochem. J.*, 2012, 442(1); 49-56). Hydrogen rich water represents one way in which molecular hydrogen can be administered to subjects. Common electrolytic and base metal methods of producing hydrogen-rich water typically result in an alkaline solution with a low $H_2$ concentration.

Creating ready-to-drink containers of $H_2$ (and thus hydrogen rich water) has its technical challenges. The equipment often used to saturate water with $H_2$ gas in sufficient volumes is both expensive and largely ineffective. When utilized, $H_2$ can be dissolved at a maximum concentration of 0.8 mM or 1.6 ppm under SATP conditions as per Henrys law. In order to retain this concentration of $H_2$ for any period of time, the container cannot have any headspace or the drink must be supersaturated to allow $H_2$ dissipation into the headspace to reach equilibrium. Even when no headspace is present, the level of $H_2$ in the container quickly falls to ~1 ppm and will continue to fall towards 0 ppm depending on the containment technology, level of headspace, and the initial concentration, as seen by other commercial products on the market. Some products retain almost no $H_2$ by the time they reach consumers. For example, the Japanese government recently evaluated consumer goods containing $H_2$ and found that most had no detectable level of $H_2$ present. (http[[://]] www.kokusen.godp/news/data/n-20161215_2.html).

Accordingly, there is a need for new compositions for producing hydrogen-rich water which maximize the dissolved hydrogen concentration.

SUMMARY OF THE INVENTION

The invention provides compositions for producing hydrogen rich water, nutraceuticals, cosmetics, pharmaceuticals, and other products. In one embodiment, the invention provides a composition, e.g., a tablet, including magnesium metal, at least one water-soluble acid, and a binding agent. The magnesium metal and at least one water-soluble acid may be present in amounts sufficient to maintain a pH of less than 7, e.g., at a specific time period after reaction, and a concentration of at least 0.5 mM $H_2$ after reaction in 50 mL water in a container e.g., a sealed or an open container, e.g., at least 0.5 mM $H_2$ after reaction in 100 mL water or at least 0.5 mM $H_2$ after reaction in 500 mL water. The composition may also include a lubricant.

In another aspect, the invention provides a composition containing magnesium metal, at least one water-soluble acid, and a binding agent, where the at least one water-soluble acid has a solubility of at least 0.01 g/mL in water. In certain embodiments, the composition disintegrates in less than 5 minutes, in particular less than 2 minutes. In certain embodiments, the composition produces at least 0.5 mM $H_2$ after contact with 50 mL water in a container at atmospheric pressure and room temperature, e.g., at least 0.5 mM $H_2$ after reaction in 100 mL water or at least 0.5 mM $H_2$ after reaction in 500 mL water. The composition may also include a lubricant.

In certain embodiments of the above aspects, the composition disintegrates in less than 5 minutes, e.g., in less than 2 minutes. In certain embodiments, the disintegrated composition maintains a pH of less than 7 at 10 minutes after being contacted with water and produces at least 0.5 mM $H_2$ after contact with 50 mL water in a container at atmospheric pressure and room temperature, e.g., at least 0.5 mM $H_2$ after reaction in 100 mL water or at least 0.5 mM $H_2$ after reaction in 500 mL water.

In another aspect, the invention provides a composition containing magnesium metal, at least one acid, and a binding agent where the composition disintegrates in less than 5 minutes to maintain a pH of less than 7 10 minutes after disintegration and at least 0.5 mM $H_2$ after contact with 50 mL water in a container at atmospheric pressure and room temperature, e.g., at least 0.5 mM $H_2$ after reaction in 100 mL water or at least 0.5 mM $H_2$ after reaction in 500 mL water.

In certain embodiments of any of the above aspects, the composition passes a pharmaceutical test for friability. In certain embodiments, the pH of the water is less than 7 at 10, 15, 20, 30, or 45 minutes after the composition is contacted with water. In certain embodiments, the pH of the water is less than 7 at least 1 hour after the composition is contacted with water. In certain embodiments, the container is open to the atmosphere. In certain embodiments, the container is closed. In certain embodiments, when the container is closed the pH remains less than 7 at 7 days after contact with water. In certain embodiments, the magnesium in the composition reacts to produce $H_2$ as it disintegrates in water, i.e., that rate of disintegration and rate of consumption of magnesium are substantially the same.

The amount of magnesium metal is, for example, 5-500 mg, e.g., 5-100 mg. The amount of acid is, for example, 30-4000 mg, e.g., 200-400 mg. In certain embodiments, the magnesium metal and acid are present in amounts sufficient to maintain a pH of between 4 and 6, and/or the magnesium metal and acid are present in amounts sufficient to produce a concentration of at least 2 mM $H_2$ in 50 mL of water in a container, e.g., a sealed or an open container, e.g., at least 2 mM $H_2$ after reaction in 100 mL water or at least 2 mM $H_2$ after reaction in 500 mL water. In certain embodiments, the magnesium metal includes flakes, e.g., −325 mesh flakes. In other embodiments, the magnesium metal is crushed, e.g., of 200 mesh or smaller. In some embodiments, the at least one acid is an edible acid. The edible acid is, for example, maleic acid, succinic add, malic add, fumaric add, formic acid, citric acid, ascorbic add, oxalic acid, tartaric acid, or a combination thereof. Exemplary edible acids are tartaric acid and malic acid. In some embodiments, the acid is a cosmetically or pharmaceutically acceptable acid. The cosmetically or pharmaceutically acceptable is, for example, acetic acid, adipic acid, alginic acid, aspartic acid, benzenesulfonic acid, benzoic acid, boric acid, butyric acid, camphoric acid, camphersulfonic acid, cyclopentanepropionic acid, digluconic acid, dodecylsulfric acid, ethanesulfonic acid, glucoheptonic acid, glycerophosphoric acid, hemisulfuric acid, heptonic acid, hexanoic acid, hydrobromic acid, hydrochloric acid, hydroiodiic acid, 2-hydroxy-ethanesulfonic acid, lactobionic acid, lactic acid, lauric acid, lauryl sulfuric acid, malonic acid, methanesulfonic acid, 2-naphthalenesulfonic acid, nicotinic acid, nitric acid, oleic acid, palmitic acid, pamoic acid, pectic acid, persulfuric acid, 3-phenylpropionic acid, phosphoric acid, picric acid, pivalic acid, propionic acid, stearic acid, sulfuric acid, tartric acid, thiocyanic acid, toluenesulfonic acid, undecanoic acid, valeric acid, or a combination thereof. Other acids include acetylsalicylic acid and 5-aminosalicylic acid. Examples of binding agents are mannitol, xylitol, maltose, dextrose, and lactose. Exemplary binding agents are dextrose and lactose. In certain embodiments, when the acid is tartaric citric, or ascorbic acid, the amount of magnesium is greater than 20 mg, e.g., at least 50 mg, or when the acid is acetylsalicylic acid and 5-aminosalicylic acid, the amount of magnesium is greater than 20 mg, e.g., at least 50 mg.

The composition may further include a nutritional supplement, e.g., a magnesium salt, sweetener, flavoring agent, coloring agent, fragrance, essential oil, water-soluble lubricant, or polysaccharide. Exemplary polysaccharides include cellulose and its derivatives, e.g., methyl cellulose or hydroxypropyl methyl cellulose, starch, apple powder, lemon powder, lime powder, grapefruit powder, psyllium husk, and pectin. Exemplary lubricants include sodium stearyl fumarate and stearic acid, in particular sodium stearyl fumarate.

The invention also provides a kit including a composition of the invention and a sealable container capable of holding between 100 mL and 2 L of water, e.g., between 150-750 mL of water. In certain embodiments, the container is double walled.

The invention further provides a method of producing hydrogen rich water by contacting a composition of the invention with water in a container so that the composition disintegrates and the magnesium metal and at least one acid react, e.g., to produce $H_2$ in the water at a concentration of at least 0.5 mM $H_2$ and maintain a pH of less than 7 at 10 minutes after disintegration at atmospheric pressure and room temperature. In certain embodiments, the water includes fruit juice, e.g., a juice containing pectin. In other embodiments, the concentration of $H_2$ is at least 1 mM. In certain embodiments, a pH of less than 7 is present at 1 hour after disintegration.

The invention further provides a method of administering hydrogen to a subject by providing the subject with a composition containing hydrogen produced from a composition of the invention, e.g., a tablet. In some embodiments, the composition containing hydrogen is a nutraceutical or topical formulation. In one embodiment, the nutraceutical is a beverage.

The invention further provides compositions enriched with hydrogen with the hydrogen gas dissolved in a carrier at a concentration of at least 0.5 mM, e.g., at a pH of less than 7. In some embodiments, the carrier is edible, cosmetic, or pharmaceutical grade. In some embodiments, the carrier is an aqueous liquid, cream, lotion, foam, paste, or gel. In some embodiments, the composition is a beverage. In certain embodiments, the maximum concentration of hydrogen is 20 mM. In some embodiments, the composition has a pH of 4-6. In one embodiment, the pH is 4.6 or lower. In some embodiments, the composition contains a nutritional supplement. In one embodiment, the nutritional supplement contains magnesium ions, potassium ions, or calcium ions. In some embodiments, the composition contains a sweetener, flavoring agent, coloring agent, fragrance, essential oil, or polysaccharide. In some embodiments, the composition contains a binding agent or water-soluble lubricant.

The invention further provides compositions for producing acidic hydrogen rich water. In one embodiment, the invention provides a composition, e.g., a tablet, including magnesium metal, an edible acid, and a binding agent. In general, the magnesium metal and edible acid are present in amounts sufficient to produce a pH of less than 7 and at least 0.5 mM $H_2$ after reaction in 500 mL of water in a sealed container. The invention also provides a kit including this composition of the invention, e.g., a tablet, and a sealable container capable of holding between 200 mL and 2 L of water, e.g., between 250-750 mL of water. In certain embodiments, the container is double walled. The invention further provides a method of producing hydrogen rich water by contacting this composition of the invention, e.g., a tablet, with water in a sealable container so that the composition, e.g., tablet, disintegrates and the magnesium metal and acid react to produce $H_2$ in the water at a concentration of at least 0.5 mM $H_2$ and a pH of less than 7, e.g., between pH is 4-6. In certain embodiments, the water comprises fruit juice, e.g., a juice containing pectin. In other embodiments, the concentration of $H_2$ is at least 1 mM. The amount of magnesium metal is, for example, 5-100 mg. In certain embodiments, the magnesium metal and edible acid are present in amounts sufficient to produce a pH of between 4 and 6, and/or the magnesium metal and edible acid are present in amounts sufficient to produce at least 2 mM $H_2$ in 500 mL of water in the sealed container. In certain embodiments, the magnesium metal is powdered, e.g., of 200 mesh or smaller. In other embodiments, the magnesium metal includes flakes, e.g., −325 mesh flakes. The edible acid is for example, selected from the group consisting of maleic acid, succinic acid, malic acid, fumaric acid, formic acid, citric acid, ascorbic acid, and oxalic acid. Examples of binding agents are mannitol, xylitol, maltose, and lactose. The composition may further include a vitamin, mineral, e.g., a magnesium salt, sweetener, flavoring agent, water soluble lubricant, or polysaccharide. Exemplary polysaccharides include methyl cellulose, starch, apple powder, lemon powder, lime powder, grapefruit powder, psyllium husk, and pectin.

Definitions

As used herein, the term "cosmetic" refers to a composition that is applied to the all or a part of the human body, e.g., hands, face, arms, or legs, for cleansing, beautifying, promoting attractiveness, or altering the appearance.

As used herein, the term "cosmetically acceptable" refers to a composition having ingredients which are acceptable for human topical use.

As used herein, the term "nutraceutical" refers to a composition having ingredients suitable at least for human consumption. Pharmaceutical grade ingredients may optionally be employed, as described in, e.g., "Remington: The Science and Practice of Pharmacy" (22nd ed.), ed. L. V. Allen, Jr., 2013, Pharmaceutical Press, Philadelphia, Pa.

As used herein, the term "passes a pharmaceutical test of friability" refers a composition that decreases in mass by at most 1% after 100 revolutions in a rotating drum of a friability tester, e.g., from Copley Scientific.

As used herein, the term "pharmaceutically acceptable" refers to a composition having ingredients which are subject to the U.S. Food and Drug Administration's pharmaceutical purity standards and further regulated by standards set by the U.S. Pharmacopoeia; this standard is 99.9% purity of a particular ingredient.

As used herein, the term "subject" refers to any animal capable of being treated topically, orally, inhalation, or intravenously with a composition containing or used to generate $H_2$. Animals include fish, reptiles, birds (e.g., chicken, turkey), and mammals. Mammals capable of being treated with compositions of the invention include primates (e.g., humans, apes), livestock (e.g., cows, pigs, sheep), beasts of burden (e.g., ox, horse, llama), and companion animals (e.g., dogs, cats).

DETAILED DESCRIPTION OF THE INVENTION

The present invention provides a composition, e.g., a tablet, that disintegrates in water to produce hydrogen rich water. By using a composition of the invention, e.g., in a ready-to-drink container, supersaturated levels of $H_2$ can be achieved, considerably more than can be achieved by addition of pure $H_2$ gas. In contrast to prior compositions, an advantage of the present invention is the ability to produce a hydrogen-enriched composition that contains a supersaturated amount of $H_2$ in an open container, i.e., at atmospheric pressure. In addition, the present invention provides compositions that pass a pharmaceutical friability test but still produce high levels of $H_2$. A further advantage of the invention is that the compositions can react quickly, e.g., in less than 2 minutes, to produce a usable, e.g., drinkable, hydrogen-enriched product having $H_2$ levels significantly higher than prior compositions.

The composition contains magnesium metal, i.e., elemental magnesium, an acid, and typically a binding agent and/or a lubricant. In water or a water-containing carrier, the magnesium metal and acid react to produce $H_2$, which dissolves in the water, and magnesium ions. An advantage of the present invention is that the composition contains sufficient acid to maintain an acidic pH during $H_2$ production. When insufficient acid is employed, the pH of the reaction will increase, e.g., until the solution is alkaline, causing the reaction to cease prior to reaching high levels of $H_2$. Without wishing to be bound by theory, at high pH, the production of $H_2$ ceases due to passivation from hydroxides and carbonates acting as ligands with the unreacted magnesium particles. When this occurs, less of the magnesium metal will react, thereby reducing the available $H_2$ produced while leaving unacceptable levels of residual solids from the composition behind in the container. Use of an acid is also advantageous, as a low pH, e.g., 4.6 or lower, aids in reducing microbial growth and therefore reducing the possibility of contamination. Thus, in certain embodiments, the invention provides compositions that produce a hydrogen-enriched product having an acidic pH during use or storage.

Magnesium Metal

Each composition contains a sufficient mass of magnesium to produce a sufficient volume of $H_2$ in the volume of water to which it is added. Accordingly, in certain embodiments, the composition contains a sufficient mass of magnesium to produce at least 0.1 mmol of $H_2$, e.g., at least 0.5 mmol, 1 mmol, 2 mmol, 3 mmol, 5 mmol, or 10 mmol of $H_2$, for example in at least 50, 75, 100, 125, 150, 175, 200, 225, 250, 500, 750, 1000, 1500, or 2000 mL of a suitable carrier, e.g. water. Suitable masses of magnesium metal include 5-1000 mg, e.g., 5-500 mg, 5-450 mg, 10-400 mg, 20-350 mg, 30-300, 40-250 mg, 50-200 mg, 60-100 mg, or about 70 mg or 80 mg of magnesium.

The physical form, e.g., size and shape, of the magnesium may be used to control the rate of reaction. Particles may be spherical, spheroidal, granular, or flaked. Smaller particles and particles with higher surface area to volume ratios react with faster kinetics. Mixtures of various sizes may also be employed. Flaked magnesium has a higher surface area to volume ratio than granular magnesium. In certain embodiments, flaked magnesium of −325 mesh may be employed in the composition. Alternatively, or in combination, larger sized magnesium or magnesium with a lower surface area to volume ratio relative to flaked magnesium may be employed. For example, magnesium of −200 mesh may be employed. In other embodiments, magnesium of +100, −100, +200, −200 (e.g., −200, +325), −325, or smaller mesh is employed. In certain embodiments, the magnesium is supplied in two sizes, e.g., −200 and −325, with the smaller size being 20-50% of the total and the larger size being the balance.

Acids

Any water-soluble acid may be employed in the invention. The acid may be edible, or otherwise of cosmetic or pharmaceutical grade. Examples of edible acids include, but are not limited to, maleic acid, succinic acid, malic acid, fumaric acid, formic acid, citric acid, ascorbic acid, oxalic acid, tartaric acid, and combinations thereof. Examples of cosmetic or pharmaceutical grade acids include acetic acid, adipic acid, alginic acid, aspartic acid, benzenesulfonic acid, benzoic acid, boric acid, butyric acid, camphoric acid, camphersulfonic acid, cyclopentanepropionic acid, digluconic acid, dodecylsulfric acid, ethanesulfonic acid, glucoheptonic acid, glycerophosphoric acid, hemisulfuric acid, heptonic acid, hexanoic acid, hydrobromic, hydrochloric acid, hydroiodiic acid, 2-hydroxy-ethanesulfonic acid, lactobionic acid, lactic acid, lauric acid, lauryl sulfuric acid, malonic acid, methanesulfonic acid, 2-naphthalenesulfonic acid, nicotinic acid, nitric acid, oleic acid, palmitic acid, pamoic acid, pectic acid, persulfuric acid, 3-phenylpropionic acid, phosphoric acid, picric acid, pivalic acid, propionic acid, stearic acid, sulfuric acid, tartric acid, thiocyanic acid, toluenesulfonic acid, undecanoic acid, valeric acid, their stereoisomers, all forms of alpha acids (e.g., α-lupulic acid), polycarboxylic acids, a Lewis acid, e.g., $AlCl_3$, and combinations thereof. Other acids include acetylsalicylic acid and 5-aminosalicylic acid. The acid will be present in an amount to react with the magnesium metal and optionally to maintain a pH of less than 7 when the composition is placed in water. It is preferable that the amount of acid chosen is sufficient to maintain a pH of less than 6, e.g., between 4 and 6, for the duration of typical beverage consumption e.g., at least 30 minutes or 1 hour. In certain embodiments, the number of moles of acid protons in the acid is at least 10, 20, 30, 40, 50, 75, or 100% greater than the number of moles of magnesium metal present. Suitable masses of the acid include 30-4000 mg, e.g., 100-1000 mg, 50-900 mg, 100-800 mg, 150-700 mg, 200-600 mg, 250-500 mg, 300-400 mg, or about 340 mg of acid. An exemplary edible acid is malic acid. Another exemplary edible acid for use in compositions of the invention is tartaric acid. Tartaric acid is highly water-soluble, having a solubility of 0.125 g/mL in water. Acids with a solubility of between about 0.01-1 g/mL, e.g., between about 0.02-0.9 g/mL, between about 0.03-0.8 g/mL, between about 0.04-0.7 g/mL, between about 0.05-0.6 g/mL, between about 0.06-0.5 g/mL, between about 0.07-0.4 g/mL, between about 0.08-0.3 g/mL, between about 0.09-0.2 g/mL, between about 0.1-0.2 g/mL, between about 0.11-0.5 g/mL, or between about 0.12-0.3 g/mL, are suitable for use in compositions of the invention. When highly water-soluble acids are used in a composition of the invention, the composition is able to quickly disintegrate upon contact with water, e.g., resulting in a more complete reaction with magnesium. This fast dissolution has the benefit of allowing the pH to remain below 7 on a timescale commensurate with beverage consumption, e.g., 1-2 hours. Other such acids, both edible and cosmetic and/or pharmaceutical grade, are known in the art.

The physical form, e.g., size and shape, of the acid may be used to control the rate of the reaction. For example, acids that are solids at room temperature, e.g., malic acid or tartaric acid, can be processed to control the size of the acid particles used to produce a composition of the invention. Smaller particles and particles with higher surface area to volume ratios react with faster kinetics. Milled acid particles may be used in a variety of mesh sizes, e.g., 40 mesh through 2500 mesh. Without being bound by theory, the rate of the dissolution of the composition is believed to be linearly dependent on mesh size. Compositions of the invention made with larger acid particles, e.g., 40-60 mesh, dissolve more slowly than those made with finer, e.g., 120 mesh through 2500 mesh acid particles. Mixtures of various sizes of acid particles may also be employed. Acid particles with controllable sizes may be produced by a number of different techniques, including, but not limited to, micronizing, ball milling, or tumbling. Other methods of producing acid particles with controllable sizes are known in the art.

Binding Agents

Any binding agent capable of disintegrating in water may be employed. Examples of binding agents include sugars such as maltose, dextrose, and lactose, and sugar alcohols such as mannitol and xylitol. Exemplary binding agents for compositions of the invention include lactose and dextrose. Other binding agents for compositions are known in the art. The amount of binding agent is, for example, between 10 and 50% of the weight of the composition, e.g., between 20-30%. Compositions of the invention may include a single binding agent, such as lactose, or may be made from a combination of two or more binding agents to control the physical properties of the composition.

The binding agent may be edible, or otherwise be of cosmetic or pharmaceutical grade as is known in the art, e.g., in Remington (Remington: The Science and Practice of Pharmacy, (22nd ed.) ed. L. V. Allen, Jr., 2013, Pharmaceutical Press, Philadelphia, Pa.).

Additional Components

The composition may also include other ingredients such as a nutritional supplement, sweetener, flavoring agent, coloring agent, fragrance, essential oil, lubricant, polysaccharide, or coating. Compositions of the invention may contain nutritional supplements, e.g., vitamins, minerals, and/or herbal extracts. For example, the composition may contain a magnesium, potassium, or calcium salt. Suitable sweeteners are known in the art, e.g., sucrose, mannose, sucralose, aspartame, saccharin, stevia, monk fruit extract, and acesulfame K. The composition may also include any food grade coloring, e.g., FD&C dyes, and/or flavoring, such as a fruit flavoring. The composition may further include an essential oil, e.g., grapeseed oil, oil of wintergreen, lavender oil. Other essential oils are known in the art. A composition may further include a fragrance, e.g. eucalyptus. A composition may also contain a polysaccharide, such as pectin, psyllium fiber, cellulose, and its derivatives, e.g., methyl cellulose or hydroxypropyl methyl cellulose, various starches, apple powder, lemon powder, lime powder, or grapefruit powder. Polysaccharides may increase the amount of $H_2$ retained after reaction. A composition may further include a water-soluble lubricant such as micronized sodium stearyl fumarate or finely prepared stearic acid, e.g., 5 micron. The composition may also have a water-penetrable coating, such as a soluble surfactant, to control the rate at which the composition dissolves. The soluble surfactant coating may be a triblock co-polymer, e.g., a poloxamer, e.g., Poloxamer 407, or a non-ionic polymer surfactant suitable for pharmaceutical use, e.g., glucosides. For example, the composition may have a coating that dissolves in under 5 minutes, e.g., under 1 minute, to allow the user to close a container before the composition begins to disintegrate and $H_2$ production begins.

Previous attempts to produce effervescent compositions, e.g., tablets, using typical lubricants such as sodium lauryl sulfate as described in U.S. Patent Publication 2016/0113865, and sodium stearyl fumarate, proved unsuccessful in producing tablets that rapidly disintegrated. This was due to the use of a higher amount of lubricant needed to form the tablets. The use of large quantities of non-micronized lubricant resulted in a tablet which had a slow disintegration time, which further created excess undissolved residues in a container and a foul taste. In contrast, compositions of the invention can make use of much less lubricant, resulting in faster reaction kinetics, a satisfactory amount of residue, and a palatable taste.

Forms of Composition

The composition may be formed into a tablet. A tablet may be of any suitable shape. For example, the tablet may be a disk, a sphere, or an ovoid. A single tablet will typically include the amount of magnesium and acid required to produce the desired amount of $H_2$ in a given volume of water, e.g., 50, 150, or 500 mL. However, a combination of multiple, smaller tablets may be employed. For example, tablets may be sized to provide sufficient $H_2$ in 250 mL, and multiple tablets may be employed for larger volumes. As the reaction of magnesium metal and acid is activated by water, the compositions of the invention will typically be stored in water-resistant packaging, such as foil or plastic. The components of the tablet will typically also be non-hygroscopic, but hygroscopic ingredients may be employed if the tablet is packaged dry in a waterproof container or wrapper. Tablets may be formed by methods known in the art.

A consideration when forming compositions of the invention into tablets is the tablet physical properties, e.g., friability. Friability is defined as the tendency for a tablet to chip, crumble or break following compression or other handling. Friability of tablets is assessed using a rotating drum and measuring the percent mass loss of tablets after rolling around the drum for a fixed number of drum revolutions. For a tablet to successfully pass friability testing, the tablet's mass can only decrease by 1% after 100 revolutions in the rotating drum. For compositions of the invention, friability is controlled by the type and grain size of acid used in the composition, the type and grain size of the binding agent, type and grain size of the lubricant, and the pressure at which the tablets were pressed in the die. The use of more finely meshed particles typically results in tablets that are highly friable. As a result of this, tablets made of finely meshed particles are often made under higher pressure to ensure they do not fall apart; this has the effect of making the tablet very hard, reducing the speed at which it can disintegrate upon contact with water. Thus, tablets using fine mesh acid may be made of a highly water-soluble acid, such as tartaric acid, in order to sustain the hydrogen generation reaction.

Other forms of the composition may also be employed. For example, the composition may be provided in the form of a powder, e.g., inside a water-soluble capsule or water-permeable bag, or small or large beads, e.g., a bath bomb, or a film.

The dissolution time of the composition, and thus the measured concentration of $H_2$, is controlled by the percent mass of the binding agent, the percent mass and type of lubricant, the acid to magnesium ratio, the physical properties of both the magnesium and the acid, e.g., mesh size and the physical conditions the composition is placed in. Compositions of the invention will typically disintegrate when contacted with water in a container in less than 5 minutes, e.g., less than 4 minutes, less than 3 minutes, less than 2 minutes, or less than 1 minute.

The temperature of the water the composition is placed in affects how quickly the composition disintegrates. Hot water will cause the composition to disintegrate quickly, but not hold a high concentration of hydrogen gas. Colder water increases the solubility of hydrogen in water, but does not cause rapid disintegration of the composition. A suitable temperature for the production of hydrogen from a composition of the invention is approximately room temperature, e.g., between 15° C.-25° C., e.g., 15° C., 16° C., 17° C., 18° C., 19° C., 20° C., 21° C., 22° C., 23° C., 24° C., or 25° C., e.g., between 59° F.-77° F., e.g., 59° F., 60° F. 61° F. 62° F. 63° F. 64° F. 65° F. 66° F. 67° F. 68° F. 69° F. 70° F. 71° F. 72° F. 73° F. 74° F. 75° F. 76° F. or 77° F.

The compositions will maintain an acidic hydrogen-enriched product, e.g., having a pH less than 7, e.g., 4-6, for at least a period of time after being contacted with water. An acidic pH may be maintained throughout the course of the typical time scale for use of the hydrogen-enriched product, such as 10 minutes after the composition is contacted by water. For example. the composition of the invention maintains a pH of less than 7 for a period of time of at least 5 minutes, e.g., 5-300 minutes, 10-250 minutes, 15-200 minutes, 20-150 minutes, 25-120 minutes, 30-100 minutes, 50-90 minutes, e.g., at least 5 minutes, at least 10 minutes, at least 15 minutes, at least 20 minutes, at least 25 minutes, at least 30 minutes, at least 35 minutes, at least 40 minutes, at least 45 minutes, at least 50 minutes, at least 55 minutes, at least 60 minutes, at least 70 minutes, at least 80 minutes, at least 90 minutes, at least 100 minutes, at least 110 minutes, at least 120 minutes, at least 130 minutes, at least 140 minutes, at least 150 minutes, at least 160 minutes, at least 170 minutes, at least 180 minutes, at least 190 minutes, at least 200 minutes, at least 250 minutes, or at least 300 minutes, e.g., at least 0.5 hours, at least 1 hour, at least 1.5 hours, at least 2 hours, at least 2.5 hours, at least 3 hours, at least at least 3.5 hours, at least 4 hours, at least 4.5 hours, or at least 5 hours. Compositions may also maintain a pH that is less than 7 for an extended period of time, e.g., at one day, seven days, 30 days, or 6 months after the composition is contacted with water. Furthermore, after this timeframe, the pH of the hydrogen enriched product may become alkaline, e.g., greater than 7.

For compositions designed for use as a cosmetic additive to a shower or bath, the rate of dissolution of the tablet is an important consideration. The composition has to dissolve slowly enough in the water in order to produce a consistent level of $H_2$ for the duration of the time in the shower or bath. An additional constraint is the thermodynamics of the dissolution reaction, as the reaction is exothermic and produces small amounts of magnesium hydroxide. If the reaction proceeds too quickly, the temperature of the resulting bath could become too hot or produce too much magnesium hydroxide; both of these effects can harm the skin. The addition of polysaccharides to the compositions has been shown to have an effect on the dissolution rate while maximizing retained $H_2$. The added polysaccharide can be a fibrous polysaccharide, such as cellulose and its derivatives, e.g., hydroxypropyl methylcellulose (HPMC, known as hypromellose). Alternatively or additionally, the addition of a soluble surfactant, such as a triblock co-polymer (e.g., Poloxamer 407) can be used to slow down the dissolution of the tablet, ensuring sufficient consumption of the magnesium and maximizing the length of time that $H_2$ is dissolved in the water.

Liquids enriched with hydrogen for use as a cosmetic or beauty spray can have a larger acid content, and the resulting composition can take advantage of the skin's naturally occurring pH of 4.5-5.2 (Lambers et al., *Int. J. Cosmet. Sci.*, 2006, 28, 359-370) to further enhance the $H_2$ concentration. $H_2$ has been shown to provide numerous benefits to the skin, and using the beauty spray as a cleanser to return the skin to its natural pH may have further health benefits.

Carriers

Compositions of the invention, e.g., tablets, are used by contacting them with a carrier such as water or other aqueous liquid. The water may be pure, e.g., deionized, or may contain other dissolved ions, e.g., spring or tap water. The water may also contain other ingredients, e.g., it can be or contain fruit juice, or may contain other dissolved gases, e.g., carbonated water, or dissolved solids, e.g., table sugar or salt. An exemplary fruit juice is lemon juice.

The volume of carrier is selected based on the application to be enriched with hydrogen. When a composition of the invention is used to produce a beverage, the volume of liquid, e.g., water or fruit juice, to be enriched is from about 100 mL to 2 L, e.g., about 100 mL, about 150 mL, about 200 mL, about 250 mL, about 300 mL, about 350 mL, about 400 mL, about 450 mL, about 500 mL, about 550 mL, about 600 mL, about 650 mL, about 700 mL, about 750 mL, about 800 mL, about 850 mL, about 900 mL, about 950 mL, about 1 L, about 1.5 L, or about 2 L. When a composition of the invention is used to produce a cosmetic product, the amount of water is from about 50 mL to 500 mL, e.g., about 50 mL, about 100 mL, about 150 mL, about 200 mL, about 250 mL, about 300 mL, about 350 mL, about 400 mL, about 450 mL, or about 500 mL.

Alternatively, the water may be present in a topical carrier such as a cream, lotion, foam, paste, or gel such that $H_2$ can be effectively delivered to the skin. Methods of producing water-soluble topical carriers are well-known in the art, e.g., as described in Remington (Remington: The Science and Practice of Pharmacy, (22nd ed.) ed. L. V. Allen, Jr., 2013, Pharmaceutical Press, Philadelphia, Pa.) and in the cosmetics industry. During or after reaction of the composition of the invention with water, the carrier can be stirred, mixed, or agitated to ensure uniform consistency.

Containers

Various containers may be used to contact the composition with a volume of water. In one embodiment, the container has a lid that may be used to seal the container, e.g., shortly after introducing a composition into a volume of water. A sealed container retains $H_2$ produced while the reaction proceeds to completion. Alternatively, $H_2$ can be produced in an open container. An example of a suitable container is a double walled, double gasketed stainless steel bottle.

Methods of Use

Compositions of the invention, e.g., tablets, are used by contacting them with a carrier that facilitates the dissolution of the composition. An exemplary carrier is water. Typically, the amount of water used to dissolve the composition is between 50 mL and 2 L, e.g., 50 mL, 150 mL, 250 mL, 355 mL, 500 mL, 750 mL, or 1 L. The user can add the composition to the water or other carrier in a sealable container and allow the reaction to proceed for 1 or more minutes depending on the temperature of the water, e.g., 1-2 minutes, at least 5 min, 10 min, 15 min, 30 min, 45 min, 60 min, 90 min, or 12 h. In certain embodiments, it is preferred that the composition react in less than 2 minutes. Preferably, the tablet and volume of water produce a concentration of at least 0.5 mM, e.g., at least 1 mM, at least 3 mM, at least 5 mM, or at least 10 mM, e.g., between 0.5-20 mM, 1-15 mM, or 5-10 mM. The inclusion of a polysaccharide, either in the composition, or in the water or carrier, e.g., in fruit juice, may increase the concentration of $H_2$ relative to the reaction in the absence of the polysaccharide, either locally near the polysaccharide or in the $H_2$ enriched composition as a whole.

As is known in the art, the consumption of hydrogen rich water aids in the treatment of various disorders including Parkinson's disease (Yoritaka et al., *BMC Neurology*, 2016, 16:66), depression (Zhang et al. *Sci. Rep.* 2016; 6:23742), periodontitis (Azuma et al. *Antioxidants (Basel)*. 2015; 4(3):513-22), diabetes type II, metabolic syndrome, chronic renal failure, inflammation, rheumatoid arthritis, interstitial cystitis, cerebral ischemia, hyperlipidemia, chronic hepatitis B, and others as described in Ichihara et al. (*Med. Gas Res*. (2015) 5:12). Accordingly, the compositions of the present invention may be consumed by subjects suffering from any of these disorders to treat the disorder or alleviate one or more symptoms thereof.

Additionally, $H_2$ has been shown to be an effective treatment for a variety of dermatological conditions. For example, when a composition of the invention is used to make a hydrogen enriched aqueous liquid, the pH of the resulting aqueous liquid can be adjusted to create a "beauty water" with a pH of 4.5-5.5, which has numerous health benefits (Lambers et al., *Int. J. Cosmet. Sci.* 2006, 28, 359-370). This "beauty water" has been used as a carrier base for ionic magnesium topical cosmetics, with the lower pH and $H_2$ content effectively facilitating magnesium absorption through the skin (*Magnes. Res.* 2016; 29(2):35-42). In another example, $H_2$ containing products have been shown to be a promising treatment for topical skin conditions such as wrinkles, atopic dermatitis, and UV-induced burns to the skin (*Mol. Cell. Toxicol.* 2013, 9(1), 15-21). For topical indications, the compositions of the invention can be directly incorporated into a dermatological carrier such as a cream, lotion, foam, paste, or gel.

Hydrogen containing products produced from in-situ generation of $H_2$ can be used to improve the health of certain livestock animals, in particular, dairy cows. It is believed that $H_2$ has potential to increase the usable lifespan and longevity of dairy cows, resulting in increased milk production.

Compositions of the invention may also be used to produce hydrogen gas that is inhaled, e.g., by breathing the gas as it evolves either from an open container or via a cannula or nasal tube.

Hydrogen-Enriched Acidic Compositions

A composition of the invention can be used in the manufacture of a number of consumer products, including, but not limited to, edible foodstuffs and nutraceuticals (e.g., beverages), and skin care products, e.g., lotions, bath bombs, or shower tablets, for effective delivery of $H_2$ to the skin. In certain embodiments, the hydrogen enriched composition is a beverage in an open container. For topical compositions, a composition of the invention can be directly incorporated into a pharmaceutical grade or cosmetic grade topical carrier such as a cream, lotion, foam, paste, or gel. Topical compositions containing $H_2$ can be soaked in, rolled, rubbed on, or sprayed directly onto the skin.

For consumer products designed to be ingested within the human body, e.g., nutraceuticals, e.g., beverages, the acid used in the production of the composition of the invention must be safely consumable, as with the edible acids described herein (e.g., malic acid or tartaric acid). The acid used in a composition of the invention to be used in the manufacture of consumer products designed for topical administration may be any pharmaceutically or cosmetically acceptable acid and its counterion that are considered "generally regarded as safe" as defined us the U.S. Food and Drug Administration for human and veterinary use. Representative acids include acetic acid, adipic acid, alginic acid, aspartic acid, benzenesulfonic acid, benzoic acid, boric acid, butyric acid, camphoric acid, camphersulfonic acid, cyclopentanepropionic acid, digluconic acid, dodecylsulfric acid, ethanesulfonic acid, glucoheptonic acid, glycerophosphoric acid, hemisulfuric acid, heptonic acid, hexanoic acid, hydrobromic, hydrochloric acid, hydroiodiic acid, 2-hydroxyethanesulfonic acid, lactobionic acid, lactic acid, lauric acid, lauryl sulfuric acid, malonic acid, methanesulfonic acid, 2-naphthalenesulfonic acid, nicotinic acid, nitric acid, oleic acid, palmitic acid, pamoic acid, pectic acid, persulfuric acid, 3-phenylpropionic acid, phosphoric acid, picric acid, pivalic acid, propionic acid, stearic acid, sulfuric acid, tartric acid, thiocyanic acid, toluenesulfonic acid, undecanoic acid, valeric acid, their stereoisomers, all forms of alpha acids (e.g., α-lupulic acid), polycarboxylic acids, a Lewis acid, e.g., $AlCl_3$, or combinations thereof. Other such acids are known in the art.

The hydrogen enriched water produced from a composition of the invention has a dissolved $H_2$ concentration between 0.5 mM and 20 mM, e.g., between 1 mM and 15 mM, between 1 and 10 mM, between 1 mM and 4 mM, between 1 mM and 3 mM, between 1 mM and 2 mM, between 1.5 mM and 4 mM, or between 2 mM and 3 mM, e.g., about 0.5 mM, about 1 mM, about 1.5 mM, about 2 mM, about 3 mM, about 4 mM, about 5 mM, about 6 mM, about 7 mM, about 8 mM, about 9 mM, about 10 mM, about 15 mM, or about 20 mM. In other embodiments, the concentration is between 1 ppm and 3 ppm, between 2 ppm and 4 ppm, between 3 ppm and 6 ppm, between 4 ppm and 8 ppm, between 5 ppm and 10 ppm, between 6 ppm and 12 ppm, or between 5 ppm and 15 ppm.

The acid content of the composition used to enrich the water with hydrogen may be sufficient to maintain a pH of less than 7, e.g., less than 6, e.g. between 4-6, while consuming a sufficient amount of the magnesium. A hydrogen enriched composition may also include a nutritional supplement, e.g., a magnesium salt, sweetener, flavoring agent, coloring agent, fragrance, essential oil, water-soluble lubricant, or a polysaccharide.

EXAMPLES

Example 1

In this example, hydrogen enriched water was created by dissolving the following two compositions in separate open containers and monitoring the evolved hydrogen concentration as a function of time.

Sample composition #1—"F6"—dissolved in 500 mL of water held at 17° C.
80 mg magnesium, −325 mesh, flaked
120 mg tartaric acid, 120 mesh
200 mg malic acid, 120 mesh
200 mg dextrose
6 mg sodium stearyl fumarate
Sample composition #2—"F1"—dissolved in 500 mL of water held at 17° C.
55 mg magnesium, −200 mesh, crushed 25 mg magnesium, −325 mesh, flaked
340 mg malic acid, 60 mesh
160 mg lactose
6 mg sodium stearyl fumarate The F6 composition containing milled 120 mesh acid particles dissolved faster (in approximately 1.75 min) than the F1 composition with larger 60 mesh grained acid particles (approximately 3.5 min). If the acids are only milled to 60 mesh in the F6 composition, the dissolution time of the tablet is approximately 3 min. Both the F6 and F1 compositions passed the minimum pharmaceutical test for friability. Further experimental data using sub-10 micron milled tartaric acid particles in the F6 composition instead of 120 mesh particles resulted in a tablet dissolution time of 45 seconds. Further, by using dextrose instead of lactose as the binder, the dissolution time per tablet decreased by approximately 30 second while allowing friability to stay within acceptable limits.

The hydrogen concentration achieved by the F6 composition after it fully disintegrated was 9 ppm. For the F1 composition, the hydrogen concentration after full disintegration was 3.5 ppm. A similar composition that did not pass friability testing provided a peak hydrogen concentration of 12 ppm after about 75 seconds. All concentration data were an average of approximately 20 individual tablets of each composition.

In a second experiment, the dissolution of a composition containing both tartaric acid and malic acid ("F35") with the following ingredients was investigated:
60 mg magnesium, −325 mesh, flaked
90 mg tartaric acid
150 mg malic acid
150 mg dextrose
6 mg sodium stearyl fumarate In identical water conditions as F1 and F6 (e.g., 500 mL water in open container at 17° C.), the concentration was 5.3 ppm after approximately 80-90 s of reaction time. The measured concentration was an average of approximately 20 tablets.

Example 2

An exemplary tablet for use in creating a hydrogen enriched ready-to-drink beverage includes the following components:
30 mg −200 mesh magnesium
30 mg −325 mesh magnesium, flaked
90 mg tartaric acid
150 mg malic acid
150 mg dextrose
5.5 mg 2500 mesh stearic acid Example 3

A tablet for use for producing a hydrogen enriched beverage in a closed container includes the following ingredients:
55 mg −200 mesh magnesium
25 mg −325 mesh magnesium, flaked
310 mg malic acid
100 mg magnesium malate
160 mg lactose
7 mg sodium stearyl fumarate
These ingredients were pressed into a tablet using a hand operated mechanical tablet press. This tablet, when dissolved in water in an airtight 500 mL container, produces $H_2$ gas. In a standard soda bottle (500 mL), the $H_2$ concentration reached 1.6 ppm (0.8 mM) within 15 minutes, 4 ppm (2 mM) within 2 hours, and exceeded 6 ppm (3 mM) within 12 hours. In a double walled, double gasketed stainless steel bottle, the concentration reached 2.8 ppm (1.4 mM) at 15 minutes, 3.8 ppm (1.9 mM) at 1 hour, and exceeded 7 ppm (3.5 mM) at 12 hours. The pH of the final solution when the tablet is added to plain water is between 4-6.

When fruit juice, including fruit juices high in pectin such as lemon, lime, apple, and orange, is used as or in addition to the liquid, the concentration of $H_2$ in the foam at the top of the liquid can exceed 20 ppm (10 mM). An increase in $H_2$ concentration was also observed with premixed pectin (Certo®) and psyllium husk.

Example 4

A tablet configured for use in a beverage for producing high concentration of $H_2$ includes the following components:
30 mg magnesium
200 mg malic acid
Sufficient amounts of both binding agent and lubricant
These ingredients may be pressed into a suitable tablet shape in a tableting die of 9-11 mm in diameter.

Example 5

A tablet configured for use in a cosmetic, shower, or bathtub use include the following components:
480 mg magnesium
720 mg tartaric acid
1200 mg malic acid
Sufficient amounts of both binding agent and lubricant to bring the tablet mass to 3600 mg.
These ingredients may be pressed into a suitable tablet shape in a tableting die of 24 mm in diameter.

Example 6

A second tablet configured for use in a cosmetic, shower, or bathtub use include the following components:
240 mg −325 mesh magnesium
360 mg 80 mesh (or lower) tartaric acid
600 mg 80 mesh (or lower) malic acid
Sufficient amounts of both binding agent and lubricant to bring the tablet mass to 1800 mg.
These ingredients may be pressed into a suitable tablet shape in a tableting die of 18 mm in diameter.

Example 7

A tablet configured for use in a beverage or cosmetic spray includes the following components:
80 mg −325 mesh magnesium
120 mg 80 mesh (or lower) tartaric acid
200 mg 80 mesh (or lower) malic acid
Sufficient amounts of both binding agent and lubricant to bring the tablet mass to 600 mg.
These ingredients may be pressed into a suitable tablet shape in a tableting die of 12 mm in diameter.

Example 8

A tablet configured for use in a beverage or cosmetic spray includes the following components:
60 mg magnesium
90 mg tartaric acid
200 mg malic acid
Sufficient amounts of both binding agent and lubricant to bring the tablet mass to 4500 mg.
These ingredients may be pressed into a suitable tablet shape in a tableting die of 12 mm in diameter.

Example 9

A tablet configured for use exclusively in a cosmetic or beauty spray includes the following components:
25-40 mg magnesium
A sufficient amount of acid, in an amount higher than the tablets used to produce an enriched beverage.
Sufficient amounts of both binding agent and lubricant
These ingredients may be pressed into a suitable tablet shape in a tableting die of 9 mm in diameter.

Example 10

An advantage of a tablet comprising finely flaked magnesium particles is that molecules of $H_2$ are evolved one at a time. When sufficient acid is present, and the mass of magnesium in the tablet is appropriate for the volume of liquid to be saturated with $H_2$ (at least 80 mg of magnesium and 300 mg total acid per 500 mL of liquid), the $H_2$ will continuously evolve, creating bubbles of $H_2$ first in the picometer size range, before they coalesce to nanometer sized bubbles, then micrometer sized bubbles, and then larger bubbles. Nanometer sized bubbles are able to saturate an aqueous solution to a higher level than bubbles of other sizes and therefore can create a higher pressure of $H_2$ in the liquid. This is because larger bubbles dissipate out of solution, but nanometer sized bubbles are more stable and the physiochemical properties of the nanometer sized bubbles are different than the individually dissolved $H_2$ molecules, which changes the relation with Henry's Law and the gas's fugacity coefficient. The increased pressure stops the reaction as per Le Chatelier's principle, leaving sub-micrometer sized magnesium flakes suspended in solution. As the $H_2$ bubbles coalesce and further dissipate, the pressure of the system drops, and an equal amount of magnesium reacts to further produce $H_2$.

This continuous reaction allows for the concentration of $H_2$ generated to be greater than 3 ppm when the composition is placed within an open container rather than a sealed bottle, e.g., under 1 atmosphere of pressure, but deliver a constant replenishment of $H_2$ to bring it the local concentration of $H_2$ to approximately 9 ppm. The speed of the tablet disintegrating and subsequent reaction of the magnesium and acid can be accelerated by choosing tablet components, e.g. coatings or binders, to control the reaction kinetics, with the reaction running to completion in no more than 4 minutes, e.g., in the range of 1-2 minutes.

The use of cold water to dissolve compositions of the invention allows for the retention of an increased concentration of hydrogen but also causes a significant slowing down of the dissolution rate of the tablet, and subsequently the overall hydrogen generation reaction. For example, in water that is just above freezing (1° C.), tablets of the invention typically need 4-5 minutes to fully dissolve. Once the water is saturated, though, the dissolved hydrogen is retained for longer in the water at a higher concentration. The use of hot water to dissolve a composition of the invention results in a significant increase in the dissolution rate and subsequently faster evolution of hydrogen. For example, in hot water, e.g., greater than room temperature, tablets of the invention typically fully dissolve is 1 minute or less. However, the rate of bubble coalescence increases dramatically with the increasing temperature, thus reducing the retention time and overall stability of the enriched water.

Using current tableting technology and capabilities, the ideal water temperature range for dissolving a tablet made from a composition of the invention is between 12-20° C., depending on the final composition of the tablet.

Example 11

A composition of the invention, e.g., a tablet, is able to dissolve and produce a semi-stable supersaturation of $H_2$ in an open, e.g., ambient pressure, container. Polysaccharides contained within the composition or present in the liquid carrier are able to form a boundary layer at the surface of the liquid. This boundary layer prevents the $H_2$ gas cloud which forms from the dissolution of the composition from quickly dissipating. For example, in a rigid container, the addition of a pH modifier, e.g., 2 tablespoons of lemon juice (which contains pectin) or vinegar, increases the available concentration of $H_2$. Use of vinegar results in a higher concentration of $H_2$ throughout the liquid. When water and lemon juice are placed in a standard soda bottle made primarily of polyethylene terephthalate (PET), the concentration of $H_2$ is increased at the top of the gas cloud by a factor of 6-7×. In an open glass bottle with the same solution of water and lemon juice, the concentration of $H_2$ gas produced increases by approximately 20%. When polysaccharides are used, a foam forms on the surface of the liquid which includes a higher concentration of $H_2$ relative to the rest of the liquid.

Open containers are able to quickly create a suspension of magnesium nanoparticles once the tablet is placed in the container. This increases the reaction rate for producing $H_2$. For example, in a tablet that fully reacts in 30 to 60 seconds, the bubbles formed at the top of the surface aggressively burst and resulted in a measured $H_2$ concentration of 1.6 ppm.

For a composition of the invention, 70-90 seconds is ideal reaction speed, often reaching 10 ppm of supersaturation within the gas cloud. The measured concentration of $H_2$ appears to linearly decrease with time, as shown in the data in Table 1, reaching the typical SATP concentration of 1.6 ppm after 8 minutes of dissolution.

TABLE 1

Measured $H_2$ concentrations after dissolving a composition of the invention

| Time of Dissolution (s) | Measured $H_2$ concertation (ppm) |
|---|---|
| 80-90 | 10 |
| 150 | 6 |
| 180 | 4.5-5 |
| 210 | 3.5-4 |
| 300 | 2.2-2.5 |
| 360 | 1.8 |
| 480 | 1.6 |

Example 12

In this example, $H_2$ enhanced water created by dissolving a composition of the invention, e.g., a tablet, in an open container was transferred into a sealable swing top glass bottle and allowed to stabilize under pressure upon further dissolution of the composition. When the sealed bottle was opened, the measured concentration of $H_2$ was 5.3 ppm.

In a further experiment, $H_2$ enhanced water created by dissolving a composition of the invention, e.g., a tablet, in an open container was transferred into a sealable PET soda bottle modified to include a pressure gauge for measuring the pressure of the interior of the bottle. As the reaction progressed, that bottle began to pressurize, creating a headspace within the bottle as $H_2$ bubbles were formed and subsequently dissipated. After 5 minutes of reaction, the measured pressure of the bottle was 25 psi, and after 30 minutes of reaction, the measured pressure of the bottle was 45 psi. At this pressure, the measured concentration of $H_2$ was 2.3 ppm.

The composition in both containers (open and sealed bottle) continued to react with micrometer particles. As the $H_2$ coalesced and dissipated, the pressure that had been contained inside the liquid transferred to the headspace, increasing the pressure in the container. Remarkably, the pressure reached by transferring the open container liquid into the PET bottle reaches and even exceeds the pressure created by dropping a tablet into a PET bottle and immediately sealing. The same tablet produces roughly 35 psi when sealed immediately due to the reaction stopping as per Le Chatelier's principle, thus also confirming the supersaturation ability of the composition.

Example 13

One variable that exerts control over the production of hydrogen from a composition of the invention is the mass of magnesium used to react with the milled acid. The relationship mass of magnesium and dissolved hydrogen concentration is approximately linear—as the amount of magnesium used increases, the amount of hydrogen produced for a fixed mass of acid increases. Table 2 presents hydrogen concentration data for a variety of magnesium masses where the acid was milled to a fine mesh (~120 mesh) particle size and a dissolution time of approximately 60-75 s.

TABLE 2

Measured $H_2$ concentrations after dissolving a composition of the invention made with ~120 mesh acid

| Mass of magnesium (mg) | Measured $H_2$ concertation (ppm) |
| --- | --- |
| 80 | 9-12 |
| 70 | N/A |
| 60 | 4-5 |
| 55 | 3 |
| 50 | 2.6-3 |

The effect of milling the acids was also studied by performing laser diffraction size distribution measurements of the bubbles produced during the dissolution reaction. Using finely milled acids, the generated bubbles exhibited a bimodal distribution, with a first mode at a diameter of approximately 50-60 nm and the second mode at a diameter of 600 nm after compensating for noise. As noted in Example 10, nanometer sized bubbles are able to saturate an aqueous solution to a higher level than bubbles of other sizes and therefore can create a higher pressure of $H_2$ in the liquid, thus confirming the importance of using finely milled acids in producing compositions for enriching water with hydrogen.

Additional testing in an open container using a tablet made with a finely milled acid produced 70 mL of hydrogen gas out of a theoretical limit of 80 mL within the first 80-90 seconds. By the second minute of the reaction, only 6 mL of hydrogen gas had escaped from the surface of the liquid in the open container.

What is claimed is:

1. A composition comprising:
   60-100 mg magnesium metal having a mesh size of −100 mesh or smaller and being spherical, spheroidal, granular, crushed, or flaked;
   200-4000 mg at least one edible acid having a mesh size of 120 mesh or smaller;
   a binding agent, wherein the binding agent is a sugar; and
   a water-soluble lubricant, wherein the composition reacts to produce $H_2$ as it disintegrates when contacted with water, wherein the composition is a tablet, wherein the tablet disintegrates in less than 4 minutes, and wherein the composition produces from 3-20 mM of dissolved and suspended $H_2$ in an open container as it disintegrates in 500 mL of water, wherein the pH of the water remains less than 7 at 30 minutes after the composition is contacted by water.

2. The composition of claim 1, wherein the composition passes a pharmaceutical test for friability.

3. The composition of claim 1, wherein the tablet disintegrates in less than 2 minutes.

4. The composition of claim 1, wherein the at least one edible acid is selected from the group consisting of maleic acid, succinic acid, malic acid, fumaric acid, formic acid, citric acid, ascorbic acid, oxalic acid, adipic acid, and tartaric acid, or a mixture thereof.

5. The composition of claim 1, wherein the at least one edible acid is tartaric acid.

6. The composition of claim 1, wherein the at least one edible acid is malic acid.

7. The composition of claim 1, wherein the at least one edible acid comprises tartaric acid and malic acid.

8. The composition of claim 1, wherein the binding agent is maltose, dextrose, or lactose.

9. The composition of claim 1, wherein the binding agent is dextrose.

10. The composition of claim 1, wherein the water-soluble lubricant is sodium stearyl fumarate or stearic acid.

11. The composition of claim 1, wherein the water-soluble lubricant is sodium stearyl fumarate.

12. The composition of claim 1, further comprising a nutritional supplement.

13. The composition of claim 12, wherein the nutritional supplement is a magnesium salt or a calcium salt.

14. The composition of claim 1, further comprising a flavoring.

15. A composition comprising:
   60-100 mg magnesium metal having a mesh size of −100 mesh or smaller and being spherical, spheroidal, granular, crushed, or flaked;
   tartaric acid having a mesh size of 120 mesh or smaller;
   malic acid having a mesh size of 120 mesh or smaller;
   dextrose; and
   sodium stearyl fumarate, wherein the composition reacts to produce $H_2$ as it disintegrates when contacted with water, wherein the composition is a tablet, wherein the tartaric acid and malic acid have a combined mass of 200-4000 mg, wherein the tablet disintegrates in less than four minutes, and wherein the composition produces from 3-20 mM of dissolved and suspended $H_2$ in an open container as it disintegrates in 500 mL of water, wherein the pH of the water remains less than 7 at 30 minutes after the composition is contacted by water.

16. The composition of claim 15, further comprising a magnesium salt, calcium salt, or flavoring.

\* \* \* \* \*